United States Patent
Maxwell

(10) Patent No.: US 7,211,061 B1
(45) Date of Patent: May 1, 2007

(54) VAGINAL CLEANSING SWAB

(76) Inventor: Johnny Duane Maxwell, 3450 Pleasant Grove Rd., White House, TN (US) 37188

( * ) Notice: Subject to any disclaimer, the term of this patent is extended or adjusted under 35 U.S.C. 154(b) by 431 days.

(21) Appl. No.: 10/664,489

(22) Filed: Sep. 17, 2003

Related U.S. Application Data

(60) Provisional application No. 60/411,199, filed on Sep. 17, 2002.

(51) Int. Cl.
*A61M 35/00* (2006.01)

(52) U.S. Cl. .......................... 604/1; D24/119
(58) Field of Classification Search ............... 604/1–3, 604/385.18; D24/119
See application file for complete search history.

(56) References Cited

U.S. PATENT DOCUMENTS

| | | | |
|---|---|---|---|
| 2,635,274 A | 4/1953 | Hatcher et al. | |
| 3,332,103 A | 7/1967 | Case | |
| 3,818,911 A | 6/1974 | Fournier | |
| D239,042 S | 3/1976 | Freake et al. | |
| 4,776,835 A | 10/1988 | Lee | |
| 4,804,362 A | 2/1989 | Enzo | |
| 4,820,259 A | 4/1989 | Stevens | |
| 5,044,040 A | 9/1991 | Tetrault | |
| 5,121,752 A | 6/1992 | Canna | |
| 5,407,423 A | 4/1995 | Yoon | |
| 5,437,628 A | 8/1995 | Fox et al. | |
| 5,439,457 A | 8/1995 | Yoon | |
| 5,531,671 A | 7/1996 | Bennett | |
| 5,676,643 A | 10/1997 | Cann et al. | |
| 5,715,559 A * | 2/1998 | Mitri | 15/118 |
| D435,101 S | 12/2000 | Graneto, III | |
| 6,789,971 B2 * | 9/2004 | Tsaur | 401/133 |

* cited by examiner

*Primary Examiner*—Tatyana Zalukaeva
*Assistant Examiner*—C. Lynne Anderson
(74) *Attorney, Agent, or Firm*—Laura M. Hagan; Kerrick, Stivers, Coyle & Van Zant

(57) ABSTRACT

The vaginal cleansing swab is utilized by females for cleansing of the vaginal area. The swab consists of an angled applicator shaft with a moisture-absorbent end piece on one end comprised of a dome-shaped tip and three disc-like portions, having a convex cross-section and with the outer diameters of the disc-like portions increasing in size toward a dome-shaped tip. The design of the vaginal cleansing swab provides for easy insertion into and cleansing of the vaginal area.

4 Claims, 4 Drawing Sheets

VAGINAL CLEANSING SWAB

This application claims priority to Provisional Patent Application No. 60/411,199 filed on Sep. 17, 2002.

SUMMARY OF THE INVENTION

The present invention relates to the field of vaginal cleansing. Currently, products offered to women in this area are limited and primarily include disposable douches. Douches have been used to clean a woman's vaginal area after her menstrual cycle, to clean away contraceptive jellies or creams, after intercourse, or to wash away built up secretions that may cause odor. However, douches have been indicated to cause problems such as an increased tendency to develop yeast infections. Currently, there are no other alternatives to the douche that can assist a woman in the cleansing of her vaginal area.

The vaginal cleansing swab provides a safe, effective way to achieve cleansing of the vaginal area without any unwanted side effects, such as increased frequency of yeast infections in the vaginal area. The swab is comprised of an applicator shaft with a moisture-absorbent end piece affixed to the first end of the shaft. The moisture-absorbent end piece has a dome-shaped tip portion and three disc-like portions, each with a different diameter, with the diameter increasing in size toward the dome-shaped tip portion of the moisture-absorbent end piece. A handle is formed from the second end of the applicator shaft and extends at an obtuse angle from the longitudinal axis of the applicator shaft. The angled handle facilitates easy insertion of the swab and the moisture-absorbent end piece into the vaginal area and works to absorb and remove vaginal secretions from the vaginal area.

DETAILED DESCRIPTION OF THE DRAWINGS

DETAILED DESCRIPTION OF THE INVENTION

Figure 1:
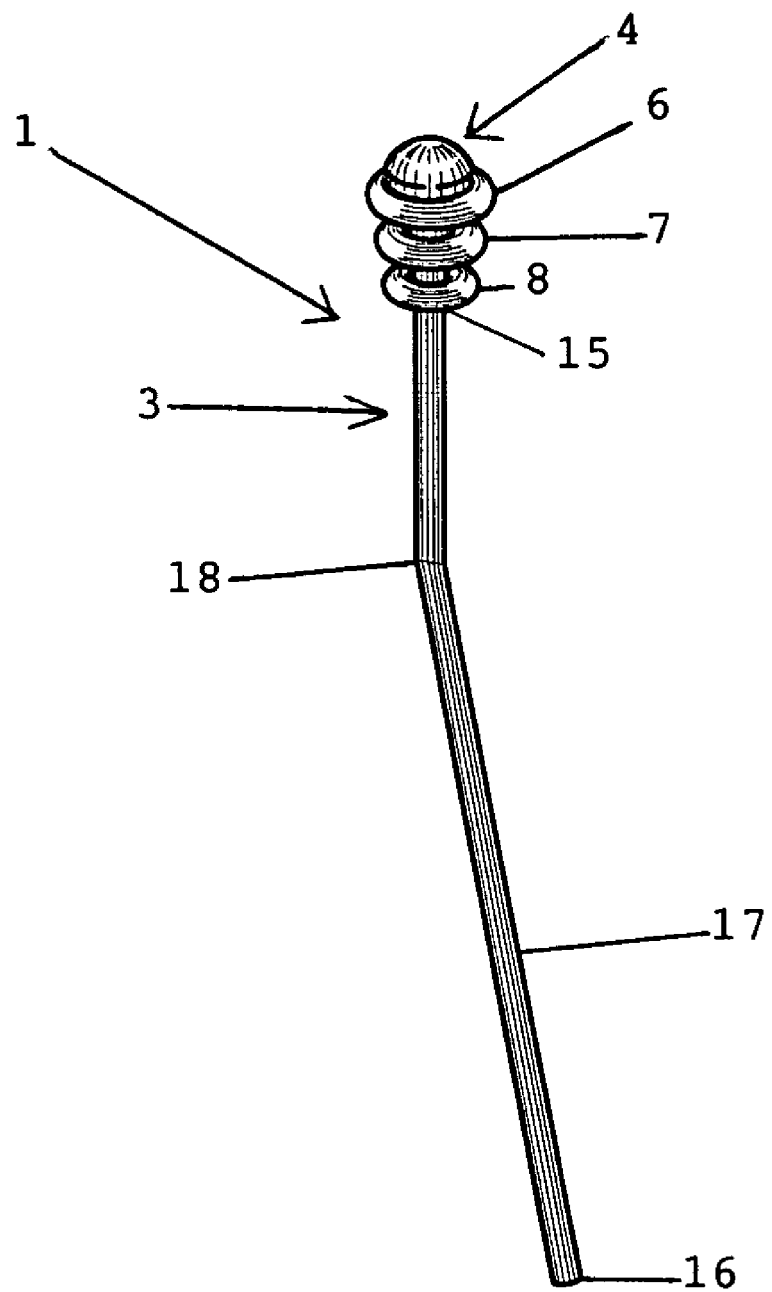
FIG. 1 is an elevated perspective view of the present invention.

Although specific terms and measurements are used in the following detailed description of the invention for the sake of clarity, the terms are intended to refer only to the particular structure of the invention selected for illustration in the drawings, and are not intended to define or limit the scope of the invention.

Figure 2:
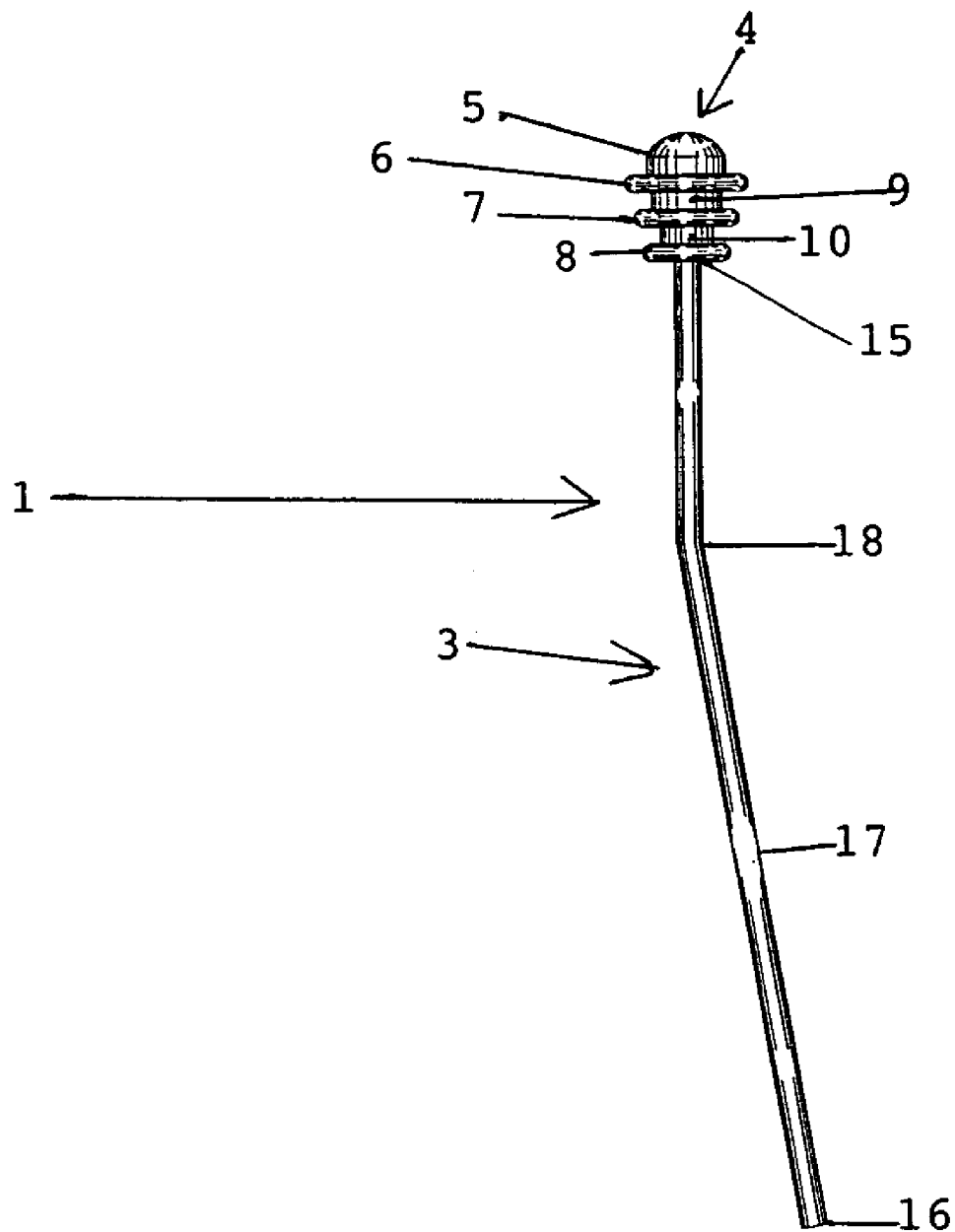
FIG. 2 is a side view of the present invention.
Figure 3:
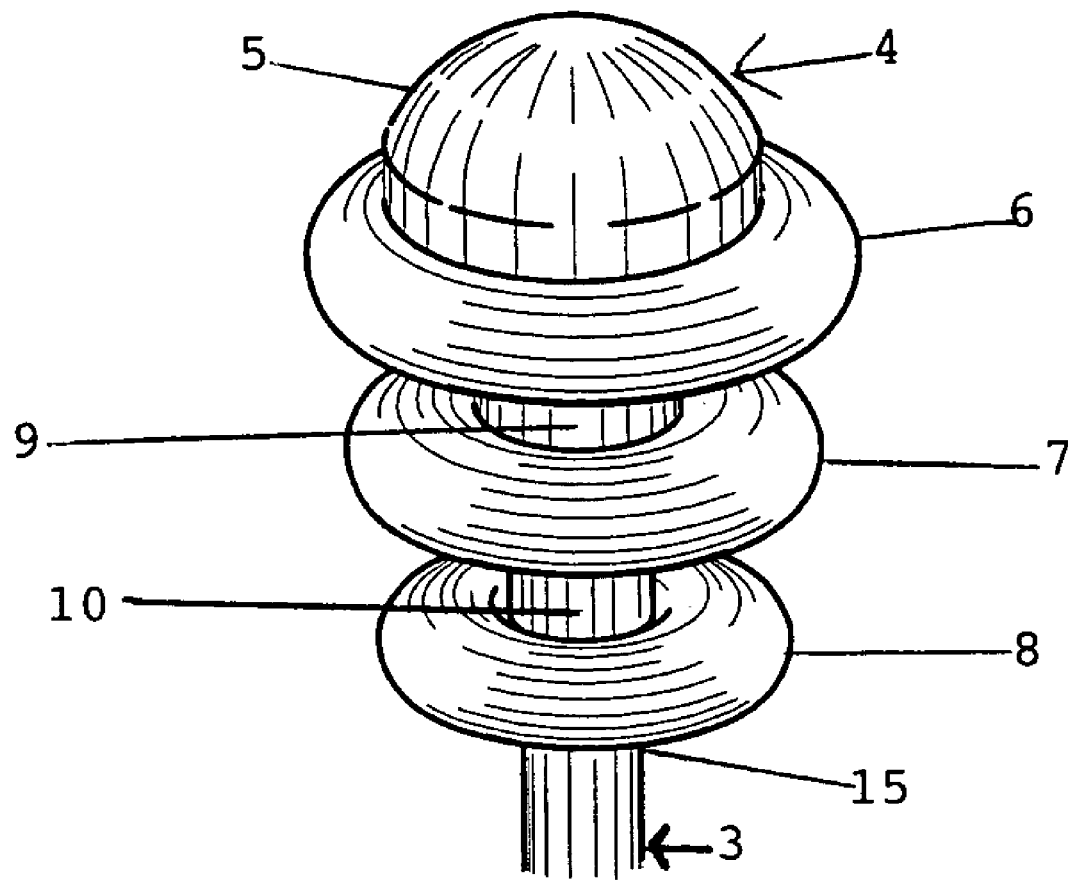
FIG. 3 is an elevated perspective view of the moisture-absorbent end piece of the present invention.
Figure 4:
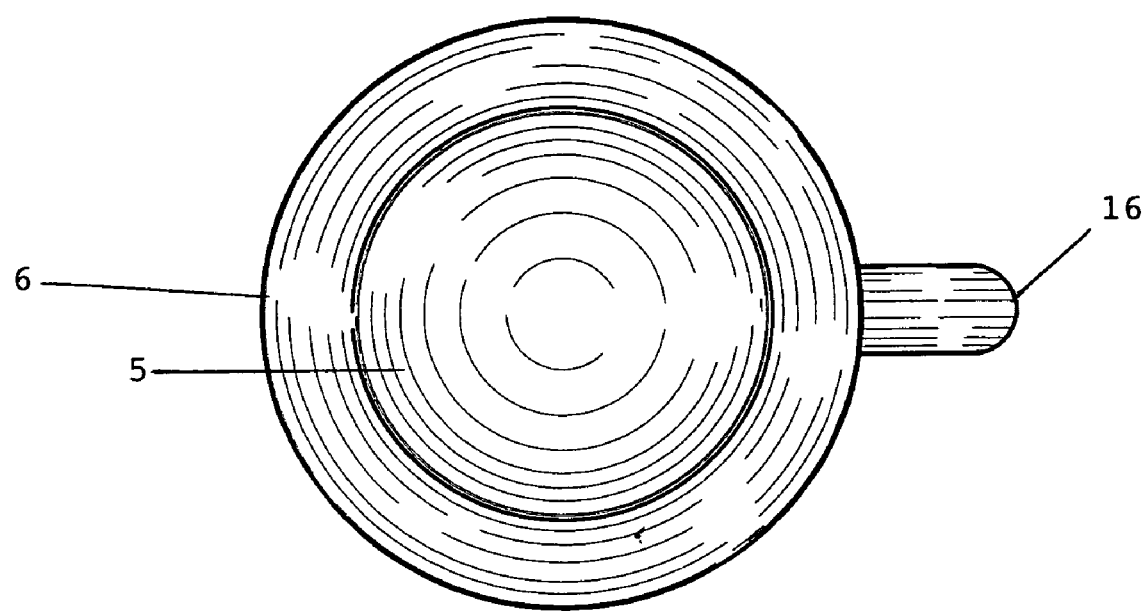
FIG. 4 is a top view of the present invention.

As is shown in FIG. 1 FIG. 2 the vaginal cleansing swab has an applicator shaft 3, which is typically cylindrical in configuration and made of a plastic, plastic-like or other suitable material. The applicator shaft 3 has a first and second end, 15,16. Attached at the first end 15 of the applicator shaft 3 is a moisture-absorbent end piece 4. The second end 16 of the applicator shaft 3 forms a handle 17, which is set at an obtuse angle from the longitudinal axis of the applicator shaft 3, and is typically constructed of the same material as the applicator shaft 3. The applicator shaft 3 forms an angle 18 at the location in which the handle 17 begins to form. This angle 18 facilitates a more comfortable insertion of the applicator shaft 3 into a woman's vaginal cavity, which has an arcuate profile.

Attached to the first end 15 of the applicator shaft 3 is a moisture-absorbent end to piece 4, which may be approximately 1¾ inches in length. The moisture-absorbent end piece 4 is secured onto the first end 15 of the applicator shaft 3 by a fusion or similar bonding technique known in the industry. The moisture-absorbent end piece 4 is comprised of a sponge-like, absorbent material. This sponge-like material may also be covered with a dry silk cover or a fine woven cotton with absorbent pores.

In the preferred embodiment, the moisture-absorbent end piece 4 has three disc-like portions, 6,7,8. These disc-like portions 6,7,8 have a convex cross-section. Each of the diameters of disc-like portions 6,7,8 increases in size toward a padded dome-shaped tip 5. The dome-shaped tip 5 sits directly on the first and largest disc-like portion 6. The first and second disc-like portions 6,7 and the second and third disc-like portion 7,8 are separated by separation areas 9,10, which are also comprised of a sponge-like, absorbent material. The outer diameter of the separation areas 9,10 can vary, as long as it is smaller than the outer diameter of the surrounding disc-like portions 6, 7, 8.

In practice, the moisture-absorbent end piece 4 of the swab 1 inserts into the vagina of the user. As the moisture-absorbent end piece 4 enters into the vaginal area of a woman, it is able to effectively and sanitarily absorb and remove fluids and secretions from the vagina. The dome-shaped tip 5 and the disc-like portions 6,7,8 all come into contact with the vaginal walls and serve to absorb unwanted creams, jellies or vaginal secretions. The disc-like portions 6,7,8 of the swab 1 serve to pull the additional fluid or secretions from the vagina of the user. The soft material utilized by the moisture-absorbent end piece 4 of the swab 1 is designed to minimize injury to the soft vaginal tissue when in use.

As the material on the moisture-absorbent end piece 4 is a sponge-like material which retains its integrity when wet, there is no danger of disintegration of the moisture-absorbent end piece 4 when inserted into the vaginal canal. The materials in which the swab 1 are composed are disposable in nature, which provides for a more sanitary means for a woman to achieve vaginal cleansing.

Other embodiments of the vaginal cleansing swab 1 include an embodiment where the moisture-absorbent end piece 4 has only a first and second disc-like portion 6,7 along with a dome-shaped tip 5. Another embodiment of the present invention would include an embodiment where the moisture-absorbent end piece 4 has only a first disc-like portion 6 and a dome-shaped tip 5. The diameters of the first and second disc-like portions 6,7, of these alternative embodiments may vary. Additionally, the disc-like portions 6,7,8 may have a outer diameter that is identical in size.

I claim:

1. A vaginal cleansing swab comprising:

an applicator shaft with a first and second end;

a moisture absorbent end piece positioned over said first end of said shaft, said moisture absorbent end piece having a dome-shaped tip and more than one projecting disc-like portions, the diameters of said projecting disc-like portions increasing in size toward the dome-shaped tip; and a first projecting disc-like portion positioned closest to said moisture absorbent end piece having a diameter larger than said dome shaped end piece; and separation areas located between said projecting disc-like portions.

2. The vaginal cleansing swab of claim 1 wherein said second end of said shaft is offset at an angle from the longitudinal axis of said shaft.

3. The vaginal cleansing swab of claim 1 wherein said separation areas are moisture absorbent.

4. The vaginal cleansing swab of claim 3 wherein the diameter of said separation areas are smaller in size than the diameters of said disc-like portions.

* * * * *